US011984218B2

United States Patent
Cai et al.

(10) Patent No.: US 11,984,218 B2
(45) Date of Patent: May 14, 2024

(54) APPARATUS, METHOD, AND NON-TRANSITORY COMPUTER-READABLE STORAGE MEDIUM FOR ENHANCING COMPUTED TOMOGRAPHY IMAGE RESOLUTION

(71) Applicant: CANON MEDICAL SYSTEMS CORPORATION, Otawara (JP)

(72) Inventors: Liang Cai, Vernon Hills, IL (US); Jian Zhou, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 421 days.

(21) Appl. No.: 17/343,519

(22) Filed: Jun. 9, 2021

(65) Prior Publication Data

US 2022/0399101 A1    Dec. 15, 2022

(51) Int. Cl.
*G06K 9/00* (2022.01)
*G06T 3/4046* (2024.01)
*G06T 5/50* (2006.01)
*G16H 30/40* (2018.01)

(52) U.S. Cl.
CPC ........... *G16H 30/40* (2018.01); *G06T 3/4046* (2013.01); *G06T 5/50* (2013.01); *G06T 2207/10081* (2013.01); *G06T 2207/20016* (2013.01)

(58) Field of Classification Search
CPC ......... G16H 30/40; G06T 3/4046; G06T 5/50; G06T 2207/10081; G06T 2207/20016
USPC ........................................................ 382/100
See application file for complete search history.

(56) References Cited

U.S. PATENT DOCUMENTS

2007/0083114 A1   4/2007  Yang et al.
2014/0205166 A1   7/2014  Benameur et al.

FOREIGN PATENT DOCUMENTS

JP        2018-190145        11/2018

OTHER PUBLICATIONS

Ma, Jiabo, et al. "PathSRGAN: multi-supervised super-resolution for cytopathological images using generative adversarial network." IEEE transactions on medical imaging 39.9 (2020): 2920-2930. (Year: 2020).*

(Continued)

*Primary Examiner* — Jonathan S Lee
(74) *Attorney, Agent, or Firm* — Oblon, McClelland, Maier & Neustadt, L.L.P.

(57) ABSTRACT

The present disclosure relates to a spatially-variant model of a point spread function and its role in enhancing medical image resolution. For instance, a method of the present disclosure comprises receiving a first medical image having a first resolution, applying a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution, and outputting the third medical image, wherein the first resolution is lower than the second resolution and the second resolution is lower than the third resolution.

12 Claims, 11 Drawing Sheets

(56) References Cited

OTHER PUBLICATIONS

Shajkofci, Adrian, and Michael Liebling. "Spatially-variant CNN-based point spread function estimation for blind deconvolution and depth estimation in optical microscopy." IEEE Transactions on Image Processing 29 (2020): 5848-5861. (Year: 2020).*
Liu, Hui, et al. "Learning deconvolutional deep neural network for high resolution medical image reconstruction." Information Sciences 468 (2018): 142-154. (Year: 2018).*
Song, Tzu-An et al. "Super-resolution PET imaging using a generative adversarial network," J Nucl Med May 1, 2019 vol. 60 No. supplement 1 576.
Biggs, David S.C., "3D Deconvolution Microscopy," *Current Protocols in Cytometry* 12.19.1-12.19.20, Apr. 2010 Published online Apr. 2010 in Wiley Interscience (www.interscience.wiley.com).
Sroubek, Filip et al, "Decomposition of Space-Variant Blur in Image Deconvolution," in *IEEE Signal Processing Letters*, vol. 23, No. 3, pp. 346-350, Mar. 2016, doi: 10.1109/LSP.2016.2519764.
Yang, Chih-Yuan, "Single-Image Super-Resolution: A Benchmark," D. Fleet et al. (Eds.): ECCV 2014, Part IV, LNCS 8692, pp. 372-386, 2014.
Park, Junyoung et al. "Computed tomography super-resolution using deep convolutional neural network,:" 2018 Phys. Med. Biol. 63 145011.

* cited by examiner

APPARATUS, METHOD, AND NON-TRANSITORY COMPUTER-READABLE STORAGE MEDIUM FOR ENHANCING COMPUTED TOMOGRAPHY IMAGE RESOLUTION

BACKGROUND

Field of the Disclosure

The present disclosure relates to a system point spread function-aided and machine learning-based approach for enhancing computed tomography image resolution.

Description of the Related Art

A persistent goal of medical imaging is to increase image quality while reducing acquisition time. This is even more pressing when radiation-based image modalities are used. One simple but disadvantageous solution to reducing radiation exposure to the patient is to reduce the image quality threshold. For this reason, many approaches attempt to convert low resolution medical images into high resolution medical images, thereby avoiding the loss of diagnostic quality that comes with reducing image quality while also reducing the amount of radiation needed to obtain the image or series of images.

Such "super-resolution" methods, however, are not applicable in every image situation. Certain radiation-based techniques, for instance, are degraded by spatial variances in image resolution. Often overlooked, these spatial variances need to be addressed in order to provide improved image quality. Moreover, such oversight renders conventional super-resolution methods less applicable as a general approach to improving image resolution and, thus, image quality. Accordingly, a new approach to enhancing image resolution is required.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus, method, and non-transitory computer-readable storage medium for enhancing computed tomography image resolution.

According to an embodiment, the present disclosure further relates to an apparatus for enhancing computed tomography image resolution, comprising processing circuitry configured to receive a first medical image having a first resolution, apply a neural network to the first medical image, the neural network including a first subset of layers and, subsequently, a second subset of layers, the first subset of layers of the neural network being configured to generate, from the first medical image, a second medical image having a second resolution and the second subset of layers of the neural network being configured to generate, from the second medical image, a third medical image having a third resolution, and output the third medical image, wherein the first resolution is lower than the second resolution and the second resolution is lower than the third resolution.

According to an embodiment, the present disclosure further relates to a method for enhancing computed tomography image resolution, comprising receiving, by processing circuitry, a first medical image having a first resolution, applying, by the processing circuitry, a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution, and outputting, by the processing circuitry, the third medical image, wherein the first resolution is lower than the second resolution and the second resolution is lower than the third resolution.

According to an embodiment, the present disclosure further relates to a non-transitory computer-readable storage medium storing computer-readable instructions that, when executed by a computer, cause the computer to perform a method for enhancing computed tomography image resolution, comprising receiving a first medical image having a first resolution, applying a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution, and outputting the third medical image, wherein the first resolution is lower than the second resolution and the second resolution is lower than the third resolution.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
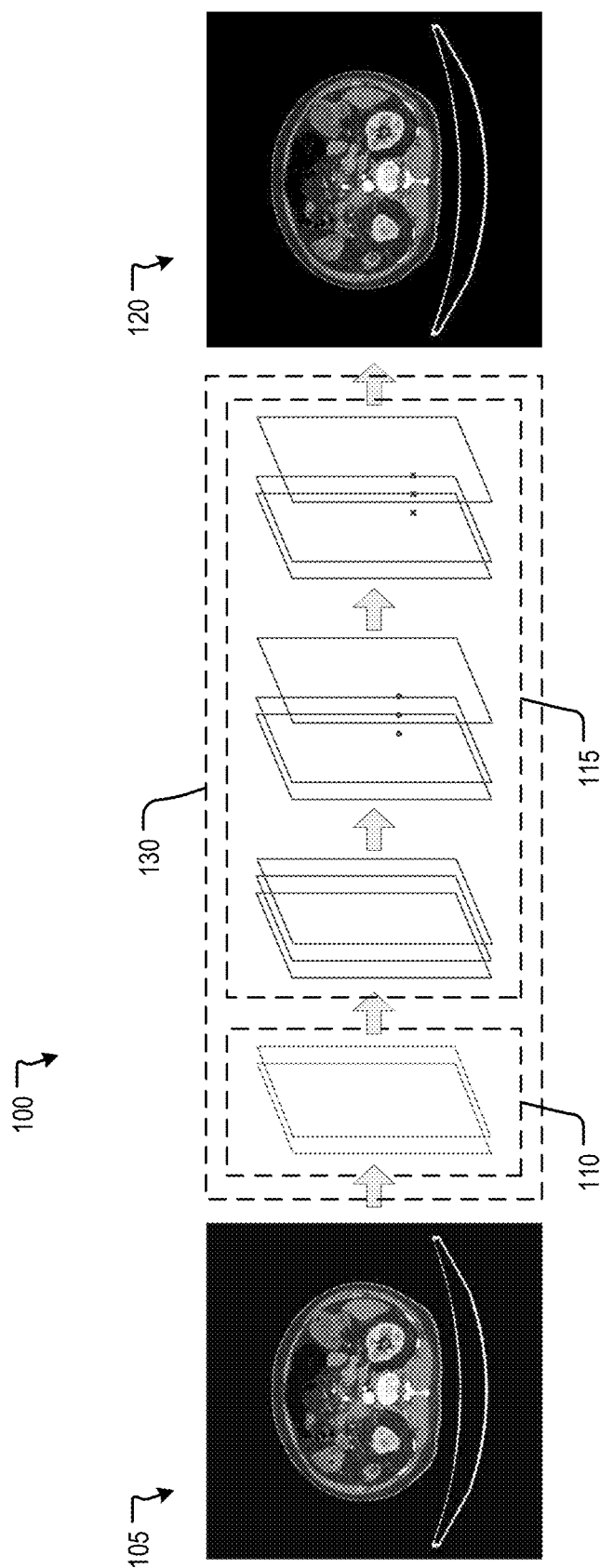
FIG. 1 is an illustrative flow diagram of a method for enhancing a computed tomography image, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

As it relates to computed tomography (CT), medical images having high spatial resolution are preferred by clinical professionals. The spatial resolution can be determined according to CT scanner geometry, CT detector pixel size, rotation view sampling rate, focal spots, reconstruction algorithms, and the like. In order to reduce image acquisition time and radiation exposure to the patient, clinicians have sought techniques for generating diagnostic quality images by converting low resolution medical images to high resolution medical image.

To this end, several conventional approaches apply "super-resolution" methods to CT data, a process that is feasible in both the sinogram domain and the image domain. Such super-resolution methods, however, are not simply implemented and still face the struggle of recovering high resolution information from low information images. For this reason, it has been a classic research topic in the field of computer vision for a number of years. This work has traditionally been summarized into four categories of super-resolution algorithms: prediction model-based models, edge-based models, image statistical-based models, and example-based models. Recently, as it relates to the image domain, convolution neural networks (CNNs) have been applied to super-resolution problems in different computer vision areas. CNNs can be used to map low resolution images to high resolution images under different neural network frameworks.

Generally, when a high resolution image is available, a low resolution image $I_x$ can be modeled as the output of the following degradation $$I_x = D(I_y; \delta) \quad (1)$$

where D denotes a degradation mapping function, $I_y$ is a corresponding high resolution image and $\delta$ is the parameters of the degradation process (e.g., the scaling factor or noise). Generally, however, the degradation process (i.e., D and $\delta$) is unknown and only low resolution images are provided (as can be imagined in the case of a diagnostic medical image). In this case, which may also be referred to as blind super-resolution, a high resolution approximation $\hat{I}_y$ of the ground truth high resolution image $I_y$ must be recovered from the low resolution image $I_x$, as follows:

$$\hat{I}_y = F(I_x; \theta) \quad (2)$$

where F is a super-resolution model and $\theta$ denotes the parameters of F.

Although the degradation process is unknown and can be affected by various factors (e.g., compression artifacts, anisotropic degradations, sensor noise and speckle noise), efforts are still made to model the degradation mapping. Most works directly model the degradation as a single downsampling operation, as follows:

$$D(I_y; \delta) = (I_y) \downarrow_s, \{s\} \subset \delta \quad (3)$$

where $\downarrow_s$ is a downsampling operation with the scaling factor s. In fact, most data sets for generic super-resolution are built based on this pattern, and the most commonly used downsampling operation is bicubic interpolation with anti-aliasing. However, other efforts model the degradation as a combination of several operations:

$$D(I_y; \delta) = (I_y \otimes k) \downarrow_s + n_\sigma, \{k, s, \sigma\} \subset \delta \quad (4)$$

where $I_y \otimes k$ represents the convolution between a blur kernel k and the high resolution image $I_y$, and $n_\sigma$ is some additive white Gaussian noise with standard deviation $\sigma$. Compared to the naive definition of Equation (3), the combinative degradation pattern of Equation (4) is closer to real-world cases and has been shown to be more beneficial for super-resolution.

To this end, the objective of super-resolution can be described as follows:

$$\hat{\theta} = \arg_\theta \min \mathcal{L}(\hat{I}_y, I_y) + \lambda \Phi(\theta) \quad (5)$$

where $\mathcal{L}(\hat{I}_y, I_y)$ represents the loss function between the generated high resolution image $\hat{I}_y$ and the ground truth image $I_y$, $\Phi(\theta)$ is the regularization term and $\lambda$ is the tradeoff parameter.

Deep learning-based super-resolution methods have also been explored in the context of CT. In these efforts, the CT image can be treated as a natural image and the deep learning-based neural network can be an end-to-end mapping architecture. In certain cases, data show that deep convolutional neural network-based super-resolution methods generate superior image quality (e.g. improves image resolution) and improve processing speed when compared with conventional methods, resulting in up-scaled images with increased diagnostic value.

However, in most CT systems, due to the "fan beam" geometry, the intrinsic spatial resolution of low resolution images and high resolution images is not exactly the same. For example, the "iso-center" area is sampled more than the peripheral area and the information is, thus, richer.

Therefore, it can be appreciated that, regardless of which of the above-described strategies is selected, such an approach is likely to ignore the spatial variations in resolution introduced by hardware constraints and limitations. For instance, the above-described Equation (4) includes a blur kernel k that is stationary. Such an approach fails to account for differences in blur in different regions of an image. In other words, such an approach fails to consider spatial variation in a point spread function of the system.

Often times, the easiest way to deal with spatial variations in the point spread function of a system is to ignore the variance. One might imagine a diffraction-limited system in which the form of the sharp core varied over the image, but the broad wings more or less stayed the same. Another approach is to segment the image and deal with the PSF of each segment locally. In this way, the PSF of each segment may be considered constant. This procedure is tedious at best, producing discontinuities when the segments are combined together, and still must find a way to represent the point spread function satisfactorily at all the locations demanded.

Accordingly, the present disclosure provides a method for generating high resolution images from low resolution images while considering spatial variations in a point spread function. By introducing a spatially-variant point spread function, intrinsic physics information can be used to augment traditional approaches within a neural network environment.

In failing to consider and account for a system point spread function, traditional neural networks are not generally applicable for spatially-variant image resolution enhancement. In other words, such a neural network, which may still be inefficient and ill-performing, would require a high volume of training data in order to generate a neural network that can be applied in such settings.

In the present disclosure, a super-resolution framework is combined with a method for accounting for the intrinsic physical relationship between high resolution CT images and low resolution CT images. In this way, the super-resolution framework of the neural network learns desirable resolution enhancement using a system point spread function (PSF) model while reducing feature dependency that would otherwise be limited by low resolution images within a training database. Moreover, by combining super-resolution with a spatially-variant PSF inside a single neural network, computational demand can be reduced and processing speed can be increased. For instance, the combined, single neural network may be executed on a graphics processing unit (GPU) of an image process system or other computing system.

The intrinsic PSF relationship between low spatial resolution images and high spatial resolution images can be approximately established as $P(X_H)=X_L$, here P can be treated as a conversion operation between a high resolution image and a low resolution image (as outlined in Equation (1)). It can be appreciated that P may be a spatially-variant model of the PSF. Conversely, as in the implementation case herein, $X_H$ is not known. Accordingly, the relationship between a low resolution image and a high resolution image can be written as $X_H=M(X_L)$, where M is the mapping operation between a low resolution image and a high resolution image. In both cases, the operations P and M can be spatially variant.

According to an embodiment, and in contrast to end-to-end network training, the neural network of the present disclosure includes the intrinsic physics determined relationship between low resolution images and high resolution images. Moreover, appreciating that P and M are spatially-variant, the network structure proposed herein is especially useful in order to be generalizable across different systems. Instead of requiring computationally-demanding training in order to generate a neural network that can be generally applied, and which may still be hard to control, the present disclosure provides physics-based intrinsic resolution difference information that can be directly integrated within the neural network via mapping operations M or P.

With reference now to the Drawings, FIG. 1 provides an illustrative flow diagram of a method for enhancing CT image resolution. While method 100 of FIG. 1 will be described with reference to CT, it can be appreciated that such a technique can be applied to any imaging modality, medical or otherwise, that has a spatially-variant PSF.

FIG. 1 provides a high-level implementation of the methods of the present disclosure. At step 105 of method 100, a first medical image having a first resolution, referred to interchangeably herein as a low resolution medical image, can be obtained from an imaging modality. The low resolution medical image may be a 2D slice(s) or a 3D image volume from any region of the body of a patient and from any perspective of the body of the patient. In an example, the low resolution medical image is a low resolution CT image obtained from, as the imaging modality, a CT scanner.

The low resolution CT image obtained at step 105 can then be provided to neural network 130 beginning at sub process 110 of method 100. The low resolution CT image, or degraded image, can be provided to a first subset of layers of the neural network 130 and converted to a second medical image having a second resolution, referred to interchangeably herein as an intermediate image or as a "coarse" high resolution image, based on a spatially-variant model of the PSF of the instance of the CT scanner. Sub process 110 will be described in greater detail with reference to FIG. 2 and FIG. 3. In an embodiment, the second resolution of the second medical image is higher than the first resolution of the first medical image.

The "coarse" high resolution image generated by the first subset of layers of the neural network 130 at sub process 110 of method 100 can then be provided to a second subset of layers of the neural network 130 at sub process 115 of method 100. The second subset of layers of the neural network 130 may comprise a super-resolution method. The super-resolution method may have a structure of a multi-layer perceptron approach or a U-net approach (which is often used for medical image segmentation and classification). After being processed according to the second subset of layers of the neural network 130, a third medical image having a third resolution, referred to interchangeably herein as a "fine" high resolution image, can be generated. In an embodiment, the third resolution of the third medical image is higher than the second resolution of the second medical image.

At step 120 of method 100, the generated "fine" resolution image of sub process 115 of method 100 can be output for medical viewing and diagnostic functions.

Figure 2:
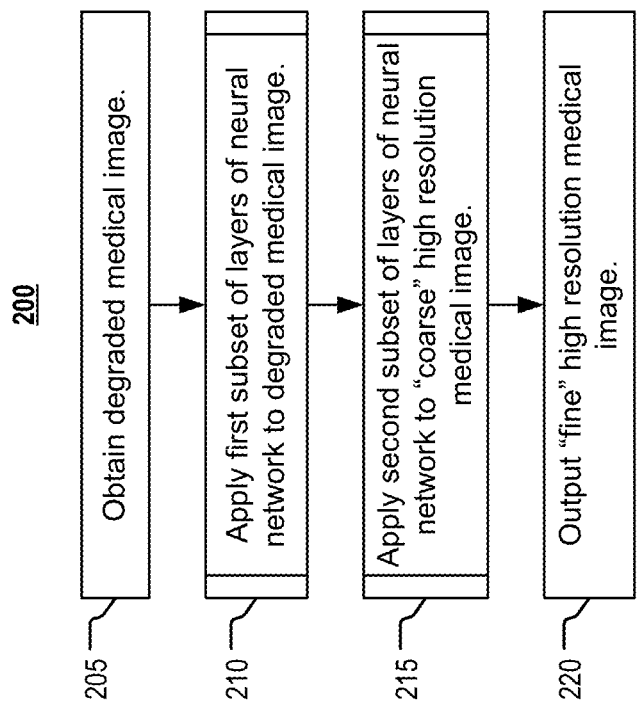
FIG. 2 is a flow diagram of a method for enhancing a computed tomography image, according to an exemplary embodiment of the present disclosure.

Method 100 will now be described as method 200 and with reference to FIG. 2. At step 205 of method 200, a degraded medical image (e.g., a CT image) can be obtained. The neural network of the present disclosure can be applied to the degraded image beginning at sub process 210. At sub process 210 of method 200, a first subset of layers of the neural network can be applied to the degraded image. The first subset of layers may be one or more layers of the neural network. The first subset of layers may utilize an intrinsic and spatially-variant model of the system PSF to generate a "coarse" high resolution image, or $X_{HR}^*$, from a low resolution image, or $X_{LR}$. The "coarse" high resolution image is an intermediate image. The converted, "coarse" high resolution image has been processed in an effort to eliminate spatial variance introduced by the imaging system, but is not upsampled in the way that would be considered a high resolution image of diagnostic quality. Such upsampling will be described with reference to sub process 215 of method 200. In other words, the "coarse" high resolution image provides an image that has overcome certain resolution limitations of the CT scanner.

In an embodiment, the relationship between the low resolution image and the "coarse" high resolution image may be explicit. For instance, the relationship may be defined as $X_{HR}^* = M(X_{LR})$, where M is a mapping operation between the low resolution image and the "coarse" high resolution image. In such a situation, the low resolution image can be directly converted to the "coarse" high resolution image by at least one matrix operation in one or more layers of the neural network.

Figure 3:
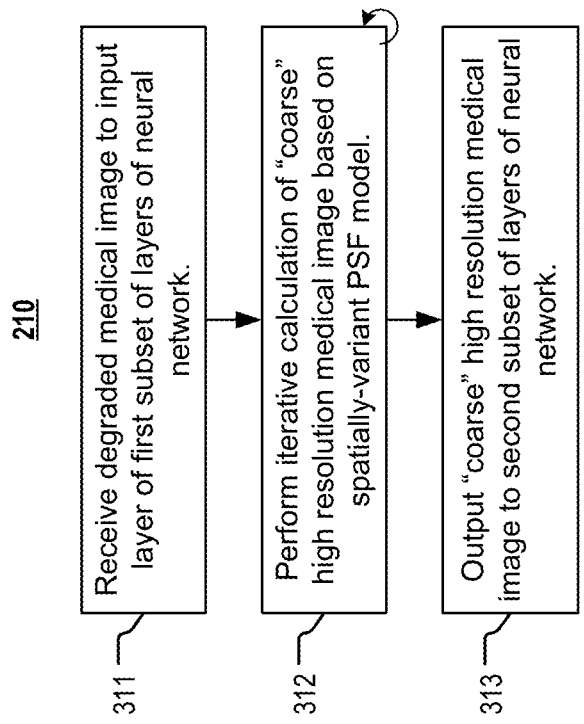
FIG. 3 is a flow diagram of a sub process of a method for enhancing a computed tomography image, according to an exemplary embodiment of the present disclosure.

In another embodiment, and with reference to FIG. 3, the relationship between the low resolution image and the "coarse" high resolution image may be inexplicit. For instance, the relationship may be defined as $P(X_{HR}^*) = X_{LR}$, where P is a mapping operation between the low resolution image and the "coarse" high resolution image. In such a situation, $X_{HR}^*$ can be iteratively solved.

For instance, since the PSF is known, P can be expressed as a set of linear equations and the "coarse" high resolution image can be obtained through an iterative process. $X_{HR}^*$ can then be solved for by, for example, the Jacobi method. In other words, iterative algorithms can form an estimate of the true object and use the PSF model to simulate how the image would appear, which can be directly compared to the observed data. An error metric can be used to determine the accuracy of the reblurred data, and the differences can be used to form a more accurate estimate of the true object. This process can be repeated for a number of iterations until a suitable result is formed. Applying too many iterations can be cause the algorithm to over-fit the observed data and cause noise to appear as a spurious structure, as would be understood by one of ordinary skill in the art.

To this end, and following receipt of the degraded medical image input to an input layer of the first subset of layers of the neural network at step 311 of sub process 210, an iterative calculation may be performed at step 312 of sub process 210, based on a spatially-variant model of the system PSF (P), to generate the "coarse" high resolution image. The iterative calculation, which comprises summations and multiplications, may be implemented as a series of matrix operations within one or more layers of the neural network and include calculating the following:

$$X_{HR}^{*(k+1)} = X_{HR}^{*(k)} + tP^T(PX_{HR}^{*(k)} - X_{LR}) \ldots$$

where t is an empirical number and k is the iteration number. In practice, and so that speed may be improved, a limited number of iterations may be performed (e.g. 5 or 6 iterations). Otherwise, stopping criteria may be determined in order to identify a satisfactory result.

In an embodiment, the spatially-variant model of the system PSF (P) can be a Gaussian-based model or similar model.

In an embodiment, and as described above, the iterative methods described above can be embodied as one or more network layers within the first subset of layers of the neural network. For instance, the iterative methods can be configured as a combination of convolutional layers, summation/subtraction layers, and the like. By integrating these methods, and the intrinsic physics PSF, in particular, within the neural network, the neural network is able to be more generally applied while utilizing computational power available to a GPU.

Alternatively, the "coarse" high resolution image can be obtained by blurring a "fine" high resolution image in order to obtain an estimated "coarse" high resolution image. The blurred image can be compared with $X_{LR}$ and a correction update therebetween can be defined and then used to create a better estimated $X_{HR}^*$ for future images.

The "coarse" high resolution image may then be output from step 313 of sub process 210 and provided to the second subset of layers of the neural network at sub process 215 of method 200.

Returning now to FIG. 2, a second subset of layers of the neural network may be applied to the generated "coarse" high resolution image at sub process 215 of method 200. In an embodiment, the second subset of layers may be based on a convolutional neural network and may be trained to generate an estimation of a "fine" high resolution image from the "coarse" high resolution image generated at sub process 210 of method 200. Training of the second subset of layers of the neural network will be further described with reference to FIG. 5. In an embodiment, the second subset of layers may be designed according to super-resolution methods.

Figure 4:
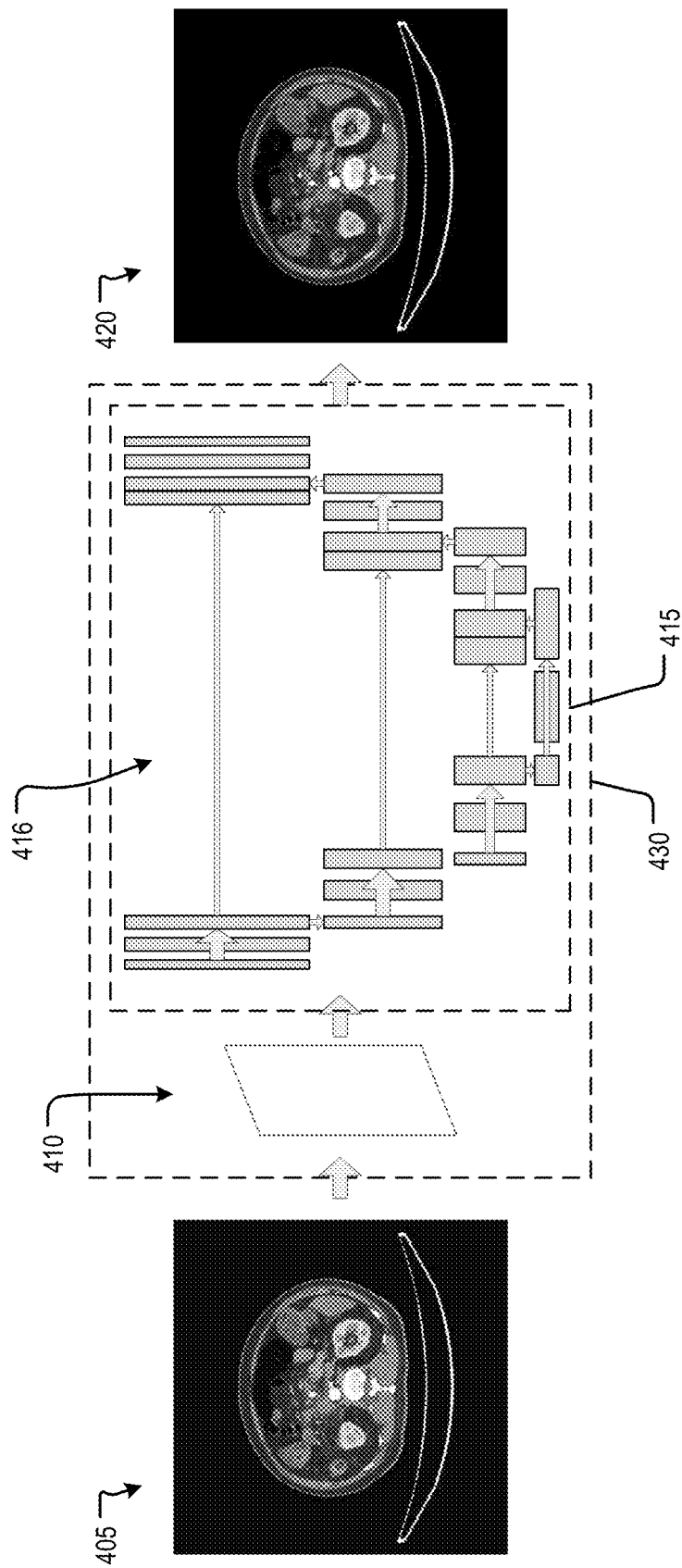
FIG. 4 is a flow diagram of an exemplary implementation phase of a method for enhancing a computed tomography image, according to an exemplary embodiment of the present disclosure.

For instance, as in FIG. 4, the super-resolution method may be based on a U-net architecture. In another instance, the super-resolution method may be based on a convolutional neural network super-resolution method selected from the group including but not limited to Super-Resolution Convolutional Neural Network (SRCNN), Fast Super-Resolution Convolutional Neural Network (FSRCNN), and Very Deep Super Resolution (VDSR). In another instance, the super-resolution method may be based on a generative adversarial network super-resolution method such as, among others, Super-Resolution Generative Adversarial Network (SRGAN). In another instance, the super-resolution method may be based on an efficient sub-pixel convolutional neural network super-resolution method (ESPCN).

The "fine" high resolution image generated from sub process 215 of method 200 can be provided to step 220 of method 200 and the "fine" high resolution image can be output as an image for viewing and, if appropriate, diagnosis.

An exemplary implementation of method 200 will now be described with reference to FIG. 4. First, a degraded medical image 405 can be received by a neural network 430. The degraded medical image 405 can be provided to a first subset of layers 410 of the neural network 430 and a "coarse" high resolution medical image, accounting for spatial variance of a model of a system PSF, can be generated according to the above described methods. The "coarse" high resolution medical image can be provided to a second subset of layers 415 of the neural network 430. The second subset of layers 415 apply a super-resolution method to the "coarse" high resolution medical to generate a "fine" high resolution medical image 420 that is suitable for diagnostic viewing.

In an embodiment, the second subset of layers 415 of the neural network 430 is based on a U-net architecture 416.

In an example, the U-net architecture 416 may have a downsampling path (left side) and an upsampling path (right side). It should be appreciated that the cartoonized U-net architecture 416 of FIG. 4 may not be to scale, as it relates to neural network layers, depth, features, and the like, and so should be considered merely representative of a type of super-resolution method that can be employed within the second subset of layers 415 of the neural network 430. The downsampling path follows the typical architecture of a convolutional network. It consists of the repeated application of two 3×3 convolutions, each followed by a rectified linear unit (ReLU) and a 2×2 pooling operation. The convolution may be an unpadded convolution and the pooling operation may be a max pooling operation with stride 2. At each downsampling step, the number of feature channels is doubled. Each step in the upsampling path consists of an upsampling of the feature map followed by a 2×2 convolution that halves the number of feature channels, a concatenation with the correspondingly cropped feature map from the contracting path, and two 3×3 convolutions, each followed by a ReLU. The cropping is necessary due to the loss of border pixels in every convolution. At the final layer of the U-net architecture 416, a 1×1 convolution is used to map each 64-component feature vector to the desired number of classes. In total, the exemplary network has 23 convolutional layers.

Figure 5:
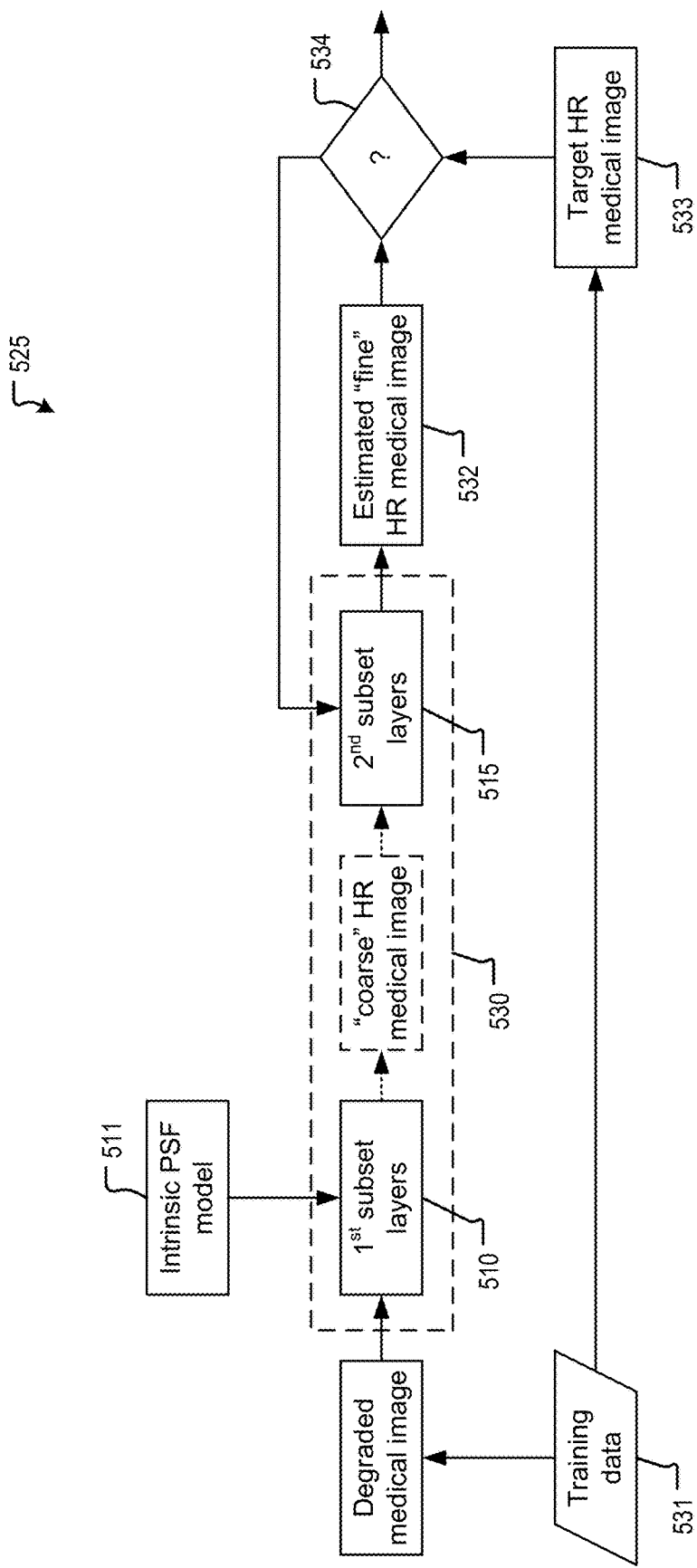
FIG. 5 is a flow diagram of a training phase of a method for enhancing a computed tomography image, according to an exemplary embodiment of the present disclosure.

FIG. 5 shows a flow diagram of process 525 describing training and optimization of, as a neural network, a convolutional neural network-based neural network, according to an exemplary embodiment of the present disclosure. The type of neural network, or artificial neural network, used can vary with application and can include residual networks, convolutional neural networks, and encoder/decoder networks, among others.

During training, a neural network 530 receives, as an input, a degraded medical image obtained from training data 531 and generates, as an output, an estimation of a "fine" high resolution medical image 532. The estimation of the "fine" high resolution medical image 532 may be minimized relative to a reference, or target high resolution medical image 533.

In an embodiment, the training data 531 may be medical images acquired from patients. As process 525 is iterative, it can be appreciated that a given instance of the training data 531 will be described with reference to a given medical image acquired from a patient. One or more of the degraded medical images and the target high resolution images can be acquired from a plurality of patients. In one training scenario, matching degraded medical images and target high resolution images are available and acquired for a given patient. In another training scenario, only degraded medical images are available. In another training scenario, target high resolution medical images are available and degraded medical images must be generated therefrom. For instance, the target high resolution medical images can be blurred or noise can be added to the medical images in order to generate the degraded medical images. JPEG and quantization artifacts can also be introduced to generate the degraded medical images. Assuming the spatial variance of the PSF has not been accounted for, no additional modifications should be required in order to generate synthetic degraded medical images. If, however, the spatial variance of the PSF has been considered previously, convolutions of the target high resolution medical images with a generalized PSF will render spatially variant image resolutions. In certain cases, an upsampling method such as bilinear interpolation or bicubic interpolation can be introduced.

Training the neural network 530, and the super-resolution methods, in particular, begins with providing the training data as an input layer to a first subset of layers 510 of the neural network 530. In an example, one or more layers of the neural network 530, including the first subset of layers 510 and second subset of layers 515, may be hidden layers. As described above with reference to FIG. 3, the first subset of layers 510 processes the degraded medical image to generate a "coarse" high resolution medical image. For instance, the relationship between the degraded medical image and the "coarse" high resolution medical image may be inexplicit. The relationship may be defined as $P(X_{HR}^*)=X_{LR}$, where P is a mapping operation between the degraded medical image and the "coarse" high resolution medical image. Accordingly, $X_{HR}^*$ can be iteratively solved. The iterative calculation may be performed on the basis of a spatially-variant model of the system PSF (P) (e.g. intrinsic PSF model 511) to generate the "coarse" high resolution medical image, as described above. The iterative calculation, which comprises summations and multiplications, may include calculating the following:

$$X_{HR}^{*(k=1)}=X_{HR}^{*(k)}+tP^T(PX_{HR}^{*(k)}-X_{LR})\ldots$$

where t is an empirical number and k is the iteration number. In practice, and so that speed may be improved, only a limited number of iterations are performed. Otherwise, stopping criteria may be determined in order to identify a satisfactory result.

The "coarse" high resolution medical image can then be provided to an 'input layer' of a second subset of layers 515 of the neural network 530. The 'input layer' can undergo convolution by a filter of a predefined size and activation. In an exemplary embodiment, the activation is a ReLU. The output of the 'input layer', or feature map, is then the input of a subsequent layer, or subsequent hidden layer, of n layers. At the first subsequent layer, the feature map is further modified via, for example, convolution, batch normalization, and activation by ReLU. In an embodiment, the output feature map of the first subsequent layer is then the input feature map for a second subsequent layer. The second subsequent layer can be a pooling layer, for example, downsampling the feature map to improve computational speed. While the first subsequent layer, the second subsequent layer, and any number a of subsequent layers may describe downsampling, the second subset of layers 515 of the neural network 530 also includes, under the assumption that only two downsampling layers exist, a series of layers that upsample the feature maps in order to estimate the "fine" high resolution medical image. For instance, the second subsequent layer may include an upsampling operation, a third subsequent layer may include a concatenation and a convolution, and a fourth subsequent layer may include a concatenation and a convolution. In this case, the output of the fourth subsequent layer then becomes the input for an output layer. The output layer may be a fully connected layer, in an example, and may describe the estimated "fine" high resolution medical image 532 for the given training data.

In an embodiment, the "fine" high resolution medical image estimation 532 from the output layer can then be compared with the concurrently obtained and/or generated target high resolution medical image 533 and a loss function can be minimized therebetween. The loss function may evaluate a difference between the estimated "fine" high resolution medical image 532 and the target high resolution medical image 533. If, upon evaluation of the loss function and comparison of the resultant value against a criterion at 534, it is determined that the criterion is met and the loss function has been minimized (i.e., there is an acceptable difference between the estimated "fine" high resolution medical image and the target high resolution medical image), the second subset of layers 515 of the neural network 530 is determined to be sufficiently trained and ready for implementation with unknown degraded data. Alternatively, if it is determined at 534 that the criterion is not met and the loss function has not been minimized, the process returns to the second subset of layers 515 of the neural network 530 and updates are made to weights/coefficients of the respective layers therein.

According to an embodiment, and as implemented at step 534 of FIG. 5, the loss function can be simply defined by a difference between the target high resolution medical image 533 and the estimated "fine" high resolution medical image 532. In other words, an optimization function defined as $$\hat{\Theta} = \arg_{\Theta} \min L(f_{\Theta}(X_{LR}|P,M), X_{HR}).$$

In the objective function, $f_{\Theta}$ defines the second subset of layers 515 of the neural network 530, L defines the loss function, $X_{LR}|P$, M represents the "coarse" high resolution image after being operated on by either of P or M, and $\hat{\Theta}$ defines the parameter set that can be optimized in order to minimize the loss function, L.

In an example, the loss function can be minimized using classic deep learning optimization methods, such as stochastic gradient descent, among others. The above-described loss function will be described with detail in a later section.

Figure 6:
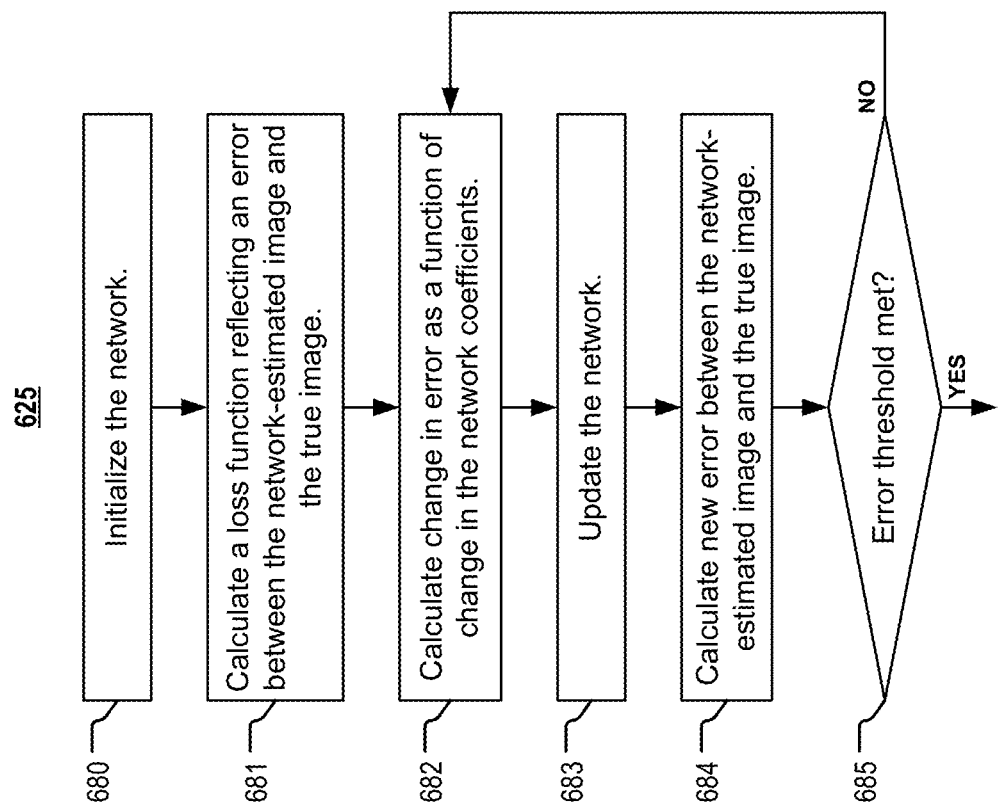
FIG. 6 is a flow diagram of training of a neural network, according to an exemplary embodiment of the present disclosure.

Now, a more detailed description of the iterative training of the second subset of layers of the neural network of FIG. 5 is provided with reference to FIG. 6. This description can be generalized, as would be understood by one of ordinary skill in the art.

FIG. 6 shows a flow diagram of one implementation of the training process 625 of the second subset of layers of the neural network performed during the "fine" high resolution medical image estimation. In training process 625, representative data from the training data database are used as training data to train the second subset of layers of the neural network. The term "data" here can refer to an image of the training image database. In an example, using training images for data, the offline training process trains the second subset of layers of the neural network using a large number of training images, which may be CT medical images generally reflective of a wide variety of patients, conditions, and body regions, or may be specifically-tailored to specific patients, conditions, and body regions. The CT medical images may be matched low resolution medical images and high resolution medical images.

In training process 625, a training database is accessed to obtain a plurality of datasets and the second subset of layers of the neural network are iteratively updated to reduce the error between the estimated image and the target image (e.g., the value produced by a loss function), wherein updating the second subset of layers of the neural network includes iteratively updating values of, for example, network coefficients, at each layer of the second subset of layers of the neural network, such that the data processed by the second subset of layers of the neural network, increasingly, matches the target high resolution medical image from the training data. In other words, the second subset of layers of the neural network infers the mapping implied by the training data, and the cost function produces an error value related to the mismatch between the data from the ground-truth data and the estimated medical image output of the current iteration of the second subset of layers of the neural network. For example, in certain implementations, the cost function can use the mean-square error to minimize the average squared error. In the case of a multilayer perceptron (MLP) neural network, the backpropagation algorithm can be used for training the network by minimizing the mean-square-error-based cost function using a (stochastic) gradient descent method. A more-detailed discussion of updating of network coefficients can be found below with reference to FIG. 7.

Training a neural network model essentially means selecting one model from the set of allowed models (or, in a Bayesian framework, determining a distribution over the set of allowed models) that minimizes the cost criterion (i.e., the error value calculated using the cost function). Generally, the second subset of layers of the neural network can be trained using any of numerous algorithms for training neural network models (e.g., by applying optimization theory and statistical estimation).

For example, the optimization method used in training the second subset of layers of the neural network to minimize the optimization function can use a form of gradient descent incorporating backpropagation to compute the actual gradients. This is done by taking the derivative of the loss function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the second subset of layers of the neural network.

With reference again to FIG. 6, the flow diagram is a non-limiting example of an implementation of training process 625 for training the second subset of layers of the neural network using the training data. The data in the training data can be from any of the training datasets within the training database.

In step 680 of training process 625, an initial guess is generated for the coefficients of the second subset of layers of the neural network. For example, the initial guess can be based on a priori knowledge of the region being imaged or one or more exemplary denoising methods, edge-detection methods, and/or blob detection methods. Additionally, the initial guess can be based on one of the LeCun initialization, an Xavier initialization, and a Kaiming initialization.

Step 681 to step 685 provides a non-limiting example of an optimization method for training the second subset of layers of the neural network. In step 681 of training process 625, an error is calculated (e.g., using a loss function or a cost function) to represent a measure of the difference (e.g., a distance measure) between the target high resolution medical image and an instantiation of an estimation of the high resolution medical image. The error can be calculated using any known loss function or distance measure between the image data, including those cost functions described above. Further, in certain implementations the error/loss function can be calculated using one or more of a hinge loss and a cross-entropy loss. In an example, the loss function can be defined as the mean square error between the output of the second subset of layers of the neural network and the target high resolution medical image, or $$\frac{1}{n}\sum_{i=1}^{n}(HR_{target} - HR_{est})^2$$

where $HR_{target}$ is the training data for the target high resolution medical image, $HR_{est}$ is the estimation of the high resolution medical image generated by the second subset of layers of the neural network, and n is the number for the training object. As described above, this loss can be minimized using optimization methods including, among others, stochastic gradient descent.

Additionally, the loss function can be combined with a regularization approach to avoid overfitting the network to the particular instances represented in the training data (as in Equation (5)). Regularization can help to prevent overfitting in machine learning problems. If trained too long, and assuming the model has enough representational power, the network will learn the features specific to that dataset, which is referred to as overfitting. In case of overfitting, the second subset of layers of the neural network becomes a poor generalization, and the variance will be large because the features vary between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the features in the training data. This goal can be achieved by, for example, early stopping, weight regularization, lasso regularization, ridge regularization, or elastic net regularization.

In certain implementations, the second subset of layers of the neural network is trained using backpropagation. Backpropagation can be used for training neural networks and is used in conjunction with gradient descent optimization methods. During a forward pass, the algorithm computes the network's prediction matrix based on the current parameters, which may be, for instance, weights/coefficients. The estimated high resolution medical image can then be input into the loss function, by which it is compared to a corresponding ground truth data (i.e., target high resolution medical image). During the backward pass, the model computes the gradient of the loss function with respect to the current parameters, after which the parameters (i.e., $\Theta$) are updated by taking a step size of a predefined size in the direction of minimized loss (e.g., in accelerated methods, such that the Nesterov momentum method and various adaptive methods, the step size can be selected to more quickly converge to optimize the loss function.

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g., Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backward passes can be performed incrementally through the respective layers of the second subset of layers of the neural network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 6, step 682 of training process 625 determines a change in the error as a function of the change in the parameters of the second subset of layers of the neural network. The delta error can be calculated (e.g., an error gradient) and this change in the error can be used to select a direction and step size for a subsequent change in the weights/coefficients of the second subset of layers of the neural network. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 683 of training process 625, a new set of coefficients are determined for the second subset of layers of the neural network. For example, the weights/coefficients can be updated using the change calculated in step 782, as in a gradient descent optimization method or an over-relaxation acceleration method.

In step 684 of process 625, a new error value is calculated using the updated weights/coefficients of the second subset of layers of the neural network.

In step 685 of process 625, predefined stopping criteria are used to determine whether the training of the second subset of layers of the neural network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations are reached. When the stopping criteria is not satisfied the training process performed in training process 625 will continue back to the start of the iterative loop by returning and repeating step 682 using the new weights and coefficients (the iterative loop includes steps 682, 683, 684, and 685). When the stopping criteria are satisfied, the training process performed in training process 625 is completed.

Figure 7:
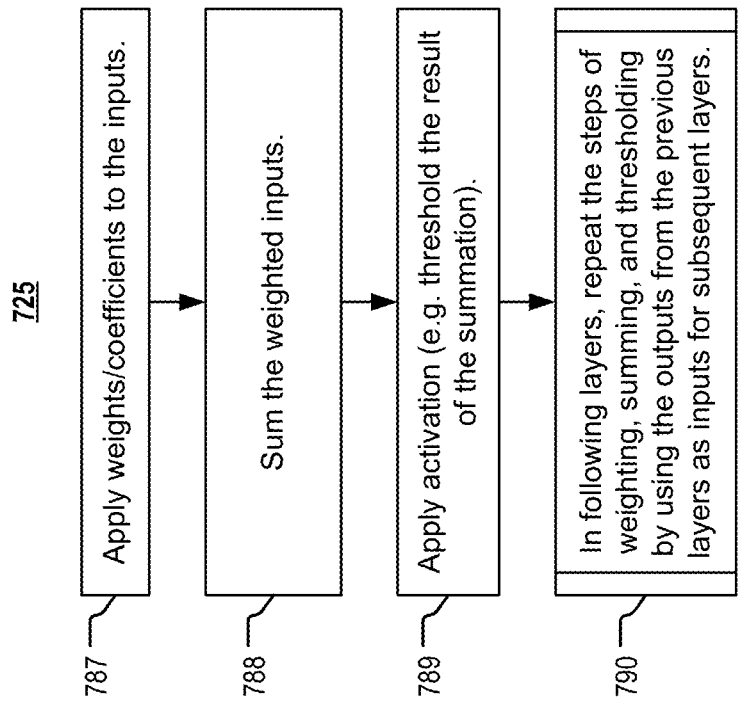
FIG. 7 is a generalized flow diagram of implementation of an artificial neural network, according to an exemplary embodiment of the present disclosure.
Figure 8:
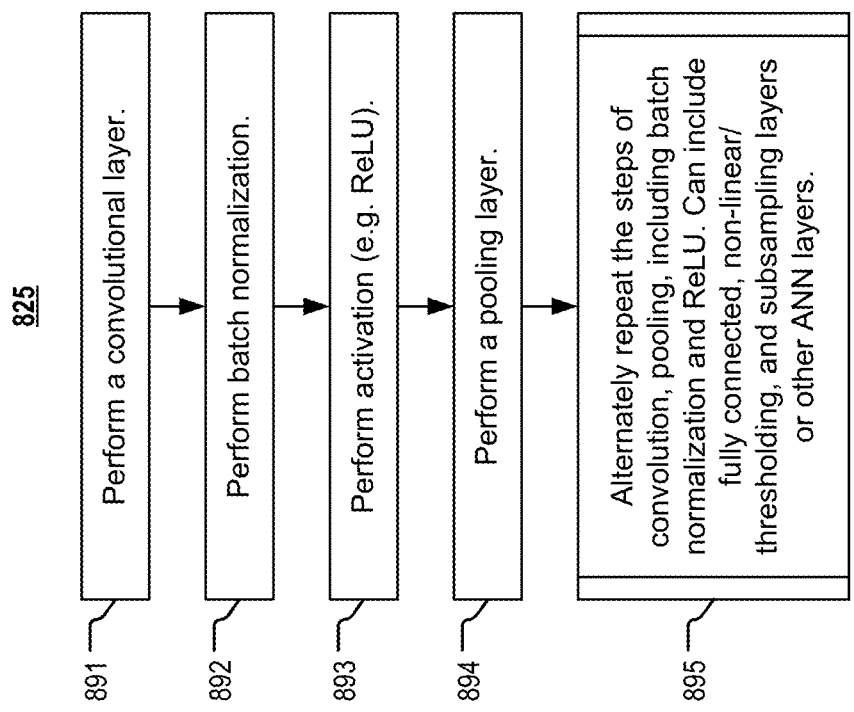
FIG. 8 is a flow diagram of implementation of a convolutional neural network, according to an exemplary embodiment of the present disclosure.

FIG. 7 and FIG. 8 show flow diagrams of implementations of portions of the second subset of layers of the neural network according to training process 625. FIG. 7 is generalized for any type of layer in a feedforward artificial neural network (ANN), including, for example, fully connected layers, whereas FIG. 8 is specific to convolutional, pooling, batch normalization, and ReLU layers, as are found in a CNN and in the 'downsampling path' of the second subset of layers of the neural network described herein. It should be appreciated that FIG. 8 represents only a portion of the second subset of layers of the neural network described herein, and the 'upsampling path' of the second subset of layers of the neural network should be separately implemented.

In step 787, the weights/coefficients corresponding to the connections between neurons (i.e., nodes) are applied to the respective inputs corresponding to, for example, the pixels of the training image.

In step 788, the weighted inputs are summed. When the only non-zero weights/coefficients connecting to a given neuron on the next layer are regionally localized in an image represented in the previous layer, the combination of step 787 and step 788 is essentially identical to performing a convolution operation.

In step 789, respective thresholds are applied to the weighted sums of the respective neurons.

In process 790, the steps of weighting, summing, and thresholding are repeated for each of the subsequent layers.

FIG. 8 shows a flow diagram of another implementation of a portion of the second subset of layers of the neural network according to training process 625. The implementation of training process 625 shown in FIG. 8 corresponds to operating on the training image at a hidden layer using a non-limiting implementation of the second subset of layers of the neural network.

In step 891, the calculations for a convolution layer are performed as discussed in the foregoing and in accordance with the understanding of convolution layers of one of ordinary skill in the art.

In step 892, following convolution, batch normalization can be performed to control for variation in the output of the previous layer, as would be understood by one of ordinary skill in the art.

In step 893, following batch normalization, activation is performed according to the foregoing description of activation and in accordance with the understanding of activation of one of ordinary skill in the art. In an example, the activation function is a rectified activation function or, for example, a ReLU, as discussed above.

In another implementation, the ReLU layer of step 893 may be performed prior to the batch normalization layer of step 892.

In step 894, the outputs from the convolution layer, following batch normalization and activation, are the inputs into a pooling layer that is performed according to the foregoing description of pooling layers and in accordance with the understanding of pooling layers of one of ordinary skill in the art.

In process 895, the steps of a convolution layer, pooling layer, batch normalization layer, and ReLU layer can be repeated in whole or in part for a predefined number of layers. Following (or intermixed with) the above-described layers, the output from the ReLU layer can be fed to a predefined number of layers within an 'upsampling path'.

Figure 9A:
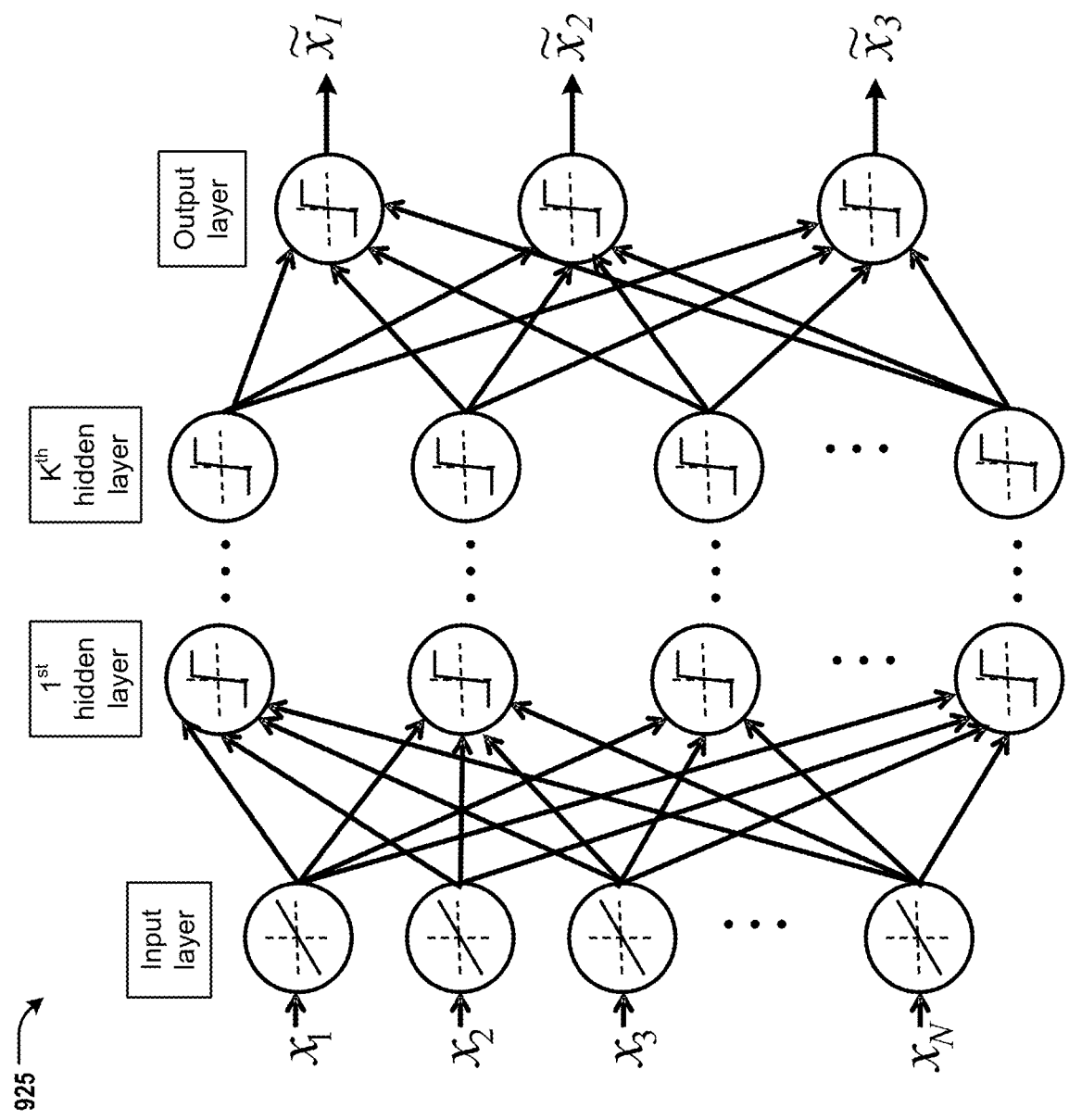
FIG. 9A is an example of a feedforward artificial neural network.
Figure 9B:
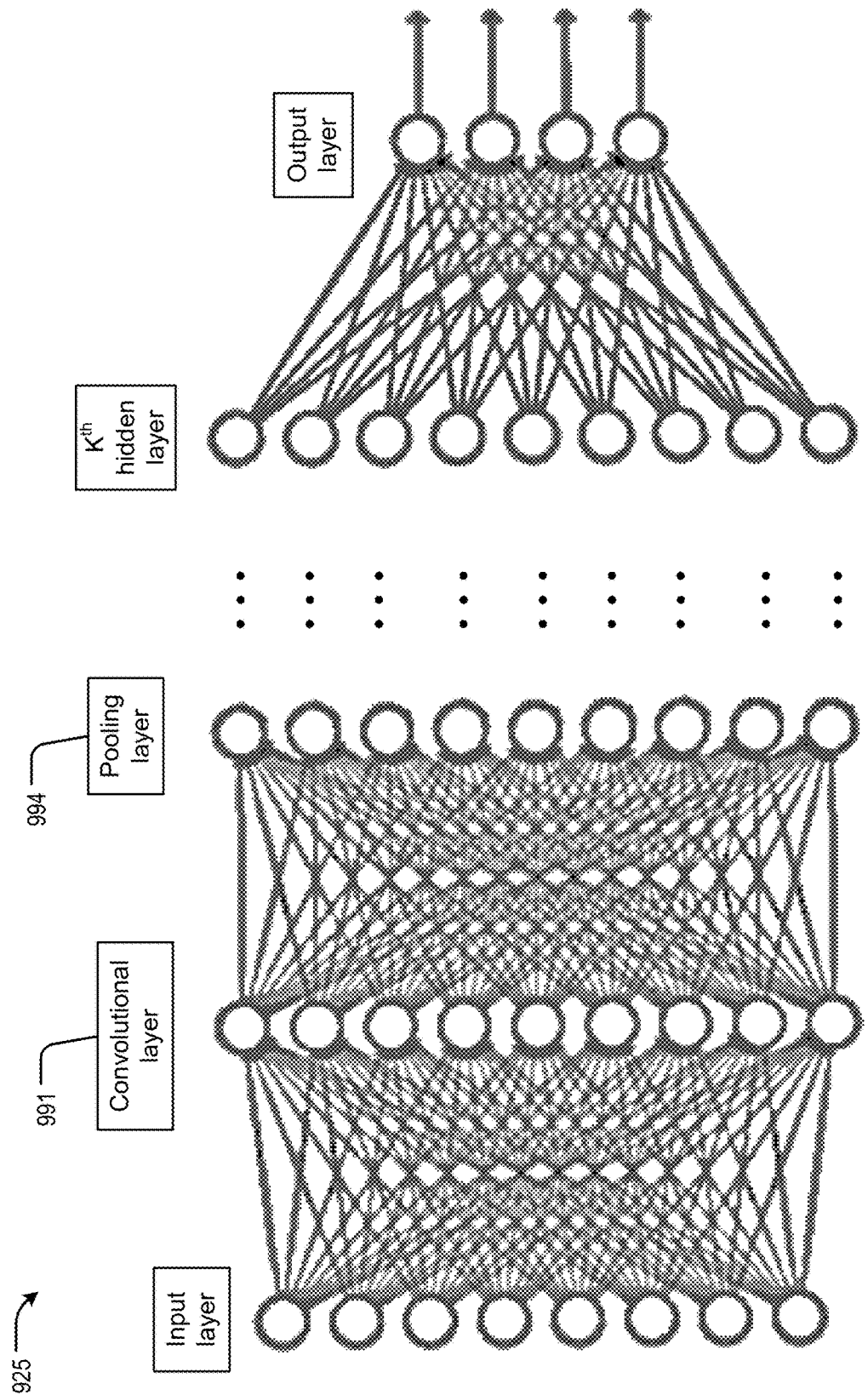
FIG. 9B is an example of a convolutional neural network, according to an exemplary embodiment of the present disclosure.

FIG. 9A and FIG. 9B show examples of the inter-connections between layers in the neural network and, in particular, the second subset of layers of the neural network. The second subset of layers of the neural network can include fully connected, convolutional, pooling, batch normalization, activation layers, concatenation layers, and upsampling layers, all of which are explained above and below. In certain preferred implementations of the second subset of layers of the neural network, convolutional layers are placed close to the input layer, whereas upsampling layers and fully connected layers, which perform the high-level reasoning, are placed further down the architecture towards the loss function. Pooling layers can be inserted after convolutions and provide a reduction lowering the spatial extent of the filters when on the downsampling path, thus reducing the amount of learnable parameters. Batch normalization layers regulate gradient distractions to outliers and accelerate the learning process. Activation functions are also incorporated into various layers to introduce non-linearity and enable the network to learn complex predictive relationships. The activation function can be a saturating activation function (e.g., a sigmoid or hyperbolic tangent activation function) or rectified activation function (e.g., ReLU discussed above). Concatenation layers and upsampling layers are also included in the upsampling path.

FIG. 9A shows an example of a general artificial neural network (ANN) having N inputs, K hidden layers, and three outputs, components of which may be incorporated herein. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The neural network of the present disclosure, and, the second subset of layers of the neural network, in particular, can have more than three layers of neurons and have as many output neurons $\tilde{x}_N$ as input neurons, wherein N is the number of, for example, pixels in the training image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can be further defined as a composition of other functions. This can be conveniently represented as a network structure, with arrows depicting the dependencies between variables, as shown in FIG. 9A and FIG. 9B. For example, the ANN can use a nonlinear weighted sum, wherein $m(x)=K(\Sigma_i w_i n_i(x))$ and where K (commonly referred to as the activation function) is some predefined function, such as the hyperbolic tangent.

In FIG. 9A (and similarly in FIG. 9B), the neurons (i.e., nodes) are depicted by circles around a threshold function. For the non-limiting example shown in FIG. 9A, the inputs are depicted as circles around a linear function and the arrows indicate directed communications between neurons. In certain implementations, the second subset of layers of the neural network is a feedforward network.

The second subset of layers of the neural network of the present disclosure operates to achieve a specific task, such as estimating a high resolution medical image, by searching within the class of functions F to learn, using a set of observations, to find $m^* \in F$, which solves the specific task in some optimal sense (e.g., the stopping criteria discussed above). For example, in certain implementations, this can be achieved by defining a loss function $C: F \to m$ such that, for the optimal solution $m^*$, $C(m^*) \leq C(m) \forall m \in F$ (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 9B shows a non-limiting example of a CNN. CNNs are a type of ANN that have beneficial properties for image processing and, therefore, have special relevancy for applications of image processing. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap to obtain a better representation of the original image. This processing pattern can be repeated over multiple layers having convolution 991 and pooling layers 994, as shown, and can include batch normalization and activation layers.

As generally applied above, following after a convolution layer 991, a CNN can include local and/or global pooling layers 994 which combine the outputs of neuron clusters in the convolution layers. Additionally, in certain implementations, the CNN can also include various combinations of convolutional and fully connected layers, with pointwise nonlinearity applied at the end of or after each layer.

Figure 10:
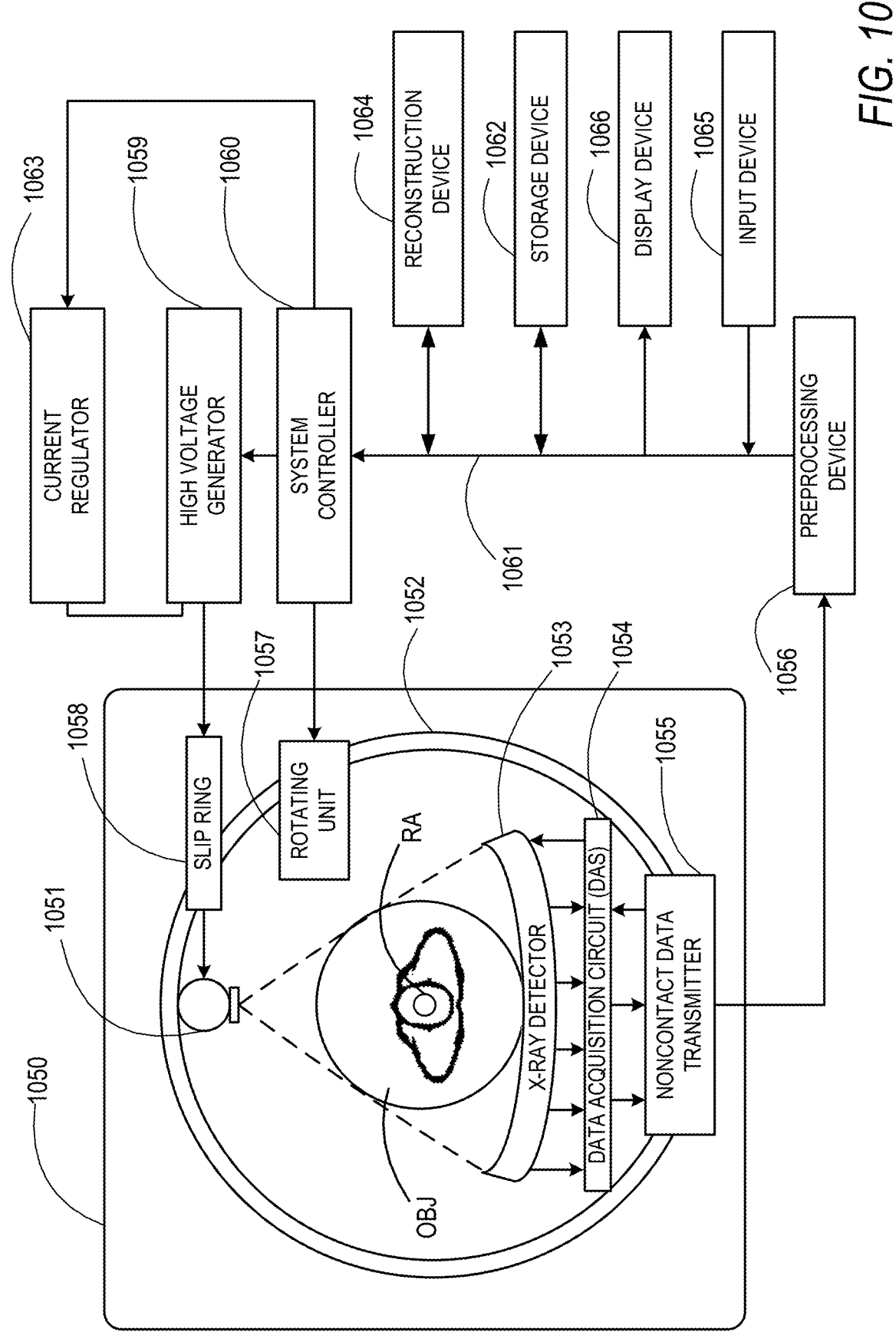
FIG. 10 is a schematic of an implementation of a CT scanner, according to an exemplary embodiment of the present disclosure.

According to an embodiment of the present disclosure, the above-described methods for patient-specific imaging protocols can be implemented as applied to data from a CT apparatus or scanner. FIG. 10 illustrates an implementation of a radiography gantry included in a CT apparatus or scanner. As shown in FIG. 10, a radiography gantry 1050 is illustrated from a side view and further includes an X-ray tube 1051, an annular frame 1052, and a multi-row or two-dimensional-array-type X-ray detector 1053. The X-ray tube 1051 and X-ray detector 1053 are diametrically mounted across an object OBJ on the annular frame 1052, which is rotatably supported around a rotation axis RA. A rotating unit 1057 rotates the annular frame 1052 at a high speed, such as 0.4 sec/rotation, while the object OBJ is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1059 that generates a tube voltage applied to the X-ray tube 1051 through a slip ring 1058 so that the X-ray tube 1051 generates X-rays. The X-rays are emitted towards the object OBJ, whose cross-sectional area is represented by a circle. For example, the X-ray tube 1051 having an average X-ray energy during a first scan that is less than an average X-ray energy during a second scan. Thus, two or more scans can be obtained corresponding to different X-ray energies. The X-ray detector 1053 is located at an opposite side from the X-ray tube 1051 across the object OBJ for detecting the emitted X-rays that have transmitted through the object OBJ. The X-ray detector 1053 further includes individual detector elements or units and may be a photon-counting detector. In the fourth-generation geometry system, the X-ray detector 1053 may be one of a plurality of detectors arranged around the object OBJ in a 360° arrangement.

The CT apparatus further includes other devices for processing the detected signals from the X-ray detector 1053. A data acquisition circuit or a Data Acquisition System (DAS) 1054 converts a signal output from the X-ray detector 1053 for each channel into a voltage signal, amplifies he signal, and further converts the signal into a digital signal. The X-ray detector 1053 and the DAS 1054 are configured to handle a predetermined total number of projections per rotation (TPPR).

The above-described data is sent to a preprocessing device 1056, which is housed in a console outside the radiography gantry 1050 through a non-contact data transmitter 1055. The preprocessing device 1056 performs certain corrections, such as sensitivity correction, on the raw data. A memory 1062 stores the resultant data, which is also called projection data at a stage immediately before reconstruction processing. The memory 1062 is connected to a system controller 1060 through a data/control bus 1061, together with a reconstruction device 1064, input device 1065, and display 1066. The system controller 1060 controls a current regulator 1063 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1051 and the X-ray detector 1053 are diametrically mounted on the annular frame 1052 and are rotated around the object OBJ as the annular frame 1052 is rotated about the rotation axis RA. In the fourth-generation geometry system, the detectors are fixedly placed around the patient and an X-ray tube rotates around the patient. In an alternative embodiment, the radiography gantry 1050 has multiple detectors arranged on the annular frame 1052, which is supported by a C-arm and a stand.

The memory 1062 can store the measurement value representative of the irradiance of the X-rays at the X-ray detector unit 1053. Further, the memory 1062 can store a dedicated program for executing the CT image reconstruction and "fine" high resolution medical image estimation methods described herein.

The reconstruction device 1064 can execute the above-referenced methods, described herein. The reconstruction device 1064 may implement, with reference to FIG. 2A and FIG. 2J, reconstruction according to one or more optimized image reconstruction parameters. Further, reconstruction device 1064 can execute pre-reconstruction processing image processing such as volume rendering processing and image difference processing as needed.

The pre-reconstruction processing of the projection data performed by the preprocessing device 1056 can include correcting for detector calibrations, detector nonlinearities, and polar effects, for example.

Post-reconstruction processing performed by the reconstruction device 1064 can include filtering and smoothing the image, volume rendering processing, and image difference processing, as needed. The image reconstruction process may implement the optimal image reconstruction parameters derived above. The image reconstruction process can be performed using filtered back projection, iterative image reconstruction methods, or stochastic image reconstruction methods. The reconstruction device 1064 can use the memory to store, e.g., projection data, forward projection training data, training images, uncorrected images, calibration data and parameters, and computer programs.

The reconstruction device 1064 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 1062 can be non-volatile, such as ROM, EPROM, EEPROM or FLASH memory. The memory 1062 can also be volatile, such as static or dynamic RAM, and a processor, such as a microcontroller or microprocessor, can be provided to manage the electronic memory as well as the interaction between the FPGA or CPLD and the memory. In an embodiment, the reconstruction device 1064 can include a CPU and a graphics processing unit (GPU) for processing and generating reconstructed images. The GPU may be a dedicated graphics card or an integrated graphics card sharing resources with the CPU, and may be one of a variety of artificial intelligence-focused types of GPUs, including NVIDIA Tesla and AMD FireStream.

Alternatively, the CPU in the reconstruction device 1064 can execute a computer program including a set of computer-readable instructions that perform the functions described herein, the program being stored in any of the above-described non-transitory electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft 10, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1066. The display 1066 can be an LCD display, CRT display, plasma display, OLED, LED or any other display known in the art.

The memory 1062 can be a hard disk drive, CD-ROM drive, DVD drive, FLASH drive, RAM, ROM or any other electronic storage known in the art.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) An apparatus for enhancing computed tomography image resolution, comprising processing circuitry configured to receive a first medical image having a first resolution, apply a neural network to the first medical image, the neural network including a first subset of layers and, subsequently, a second subset of layers, the first subset of layers of the neural network being configured to generate, from the first medical image, a second medical image having a second resolution and the second subset of layers of the neural network being configured to generate, from the second medical image, a third medical image having a third resolution, and output the third medical image, wherein the first resolution is lower than the second resolution and the second resolution is lower than the third resolution.

(2) The apparatus according to (1), wherein the first subset of layers of the neural network generates the second medical image based on an intrinsic physics-based model of a point spread function.

(3) The apparatus according to either of (1) or (2), wherein the intrinsic physics-based model of the point spread function is a spatially-variant model.

(4) The apparatus according to any one (1) to (3), wherein the spatially-variant model is a Gaussian-based model.

(5) The apparatus according to any one of (1) to (4), wherein the second subset of layers of the neural network is based on a convolutional neural network.

(6) A method for enhancing computed tomography image resolution, comprising receiving, by processing circuitry, a first medical image having a first resolution, applying, by the processing circuitry, a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution, and outputting, by the processing circuitry, the third medical image, wherein the first resolution is lower than the second resolution and the second resolution is lower than the third resolution.

(7) The method according to (6), wherein the first subset of layers of the neural network generates the second medical image based on an intrinsic physics-based model of a point spread function.

(8) The method according to either (6) or (7), wherein the intrinsic physics-based model of the point spread function is a spatially-variant model.

(9) The method according to any one of (6) to (8), wherein the spatially-variant model is a Gaussian-based model.

(10) The method according to any one of (6) to (9), wherein the second subset of layers of the neural network is based on a convolutional neural network.

(11) A non-transitory computer-readable storage medium storing computer-readable instructions that, when executed by a computer, cause the computer to perform a method for enhancing computed tomography image resolution, comprising receiving a first medical image having a first resolution, applying a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution, and outputting the third medical image, wherein the first resolution is lower than the second resolution and the second resolution is lower than the third resolution.

(12) The non-transitory computer-readable storage medium according to (11), wherein the first subset of layers of the neural network generates the second medical image based on an intrinsic physics-based model of a point spread function.

(13) The non-transitory computer-readable storage medium according to either (11) or (12), wherein the intrinsic physics-based model of the point spread function is a spatially-variant model.

(14) The non-transitory computer-readable storage medium according to any one of (11) to (13), wherein the spatially-variant model is a Gaussian-based model.

(15) The non-transitory computer-readable storage medium according to any one of (11) to (14), wherein the second subset of layers of the neural network is based on a convolutional neural network.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for enhancing computed tomography image resolution, comprising:

processing circuitry configured to
- receive a first medical image having a first resolution,
- apply a neural network to the first medical image, the neural network including a first subset of layers and, subsequently, a second subset of layers, the first subset of layers of the neural network being configured to generate, from the first medical image, a second medical image having a second resolution and the second subset of layers of the neural network being configured to generate, from the second medical image, a third medical image having a third resolution, and
- output the third medical image,
- wherein the first resolution is lower than the second resolution, the second resolution is lower than the third resolution, and the first subset of layers of the neural network generates the second medical image based on an intrinsic physics-based model of a point spread function.

2. The apparatus according to claim 1, wherein the intrinsic physics-based model of the point spread function is a spatially-variant model.

3. The apparatus according to claim 2, wherein the spatially-variant model is a Gaussian-based model.

4. The apparatus according to claim 1, wherein the second subset of layers of the neural network is based on a convolutional neural network.

5. A method for enhancing computed tomography image resolution, comprising:
- receiving, by processing circuitry, a first medical image having a first resolution;
- applying, by the processing circuitry, a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution; and
- outputting, by the processing circuitry, the third medical image,
- wherein the first resolution is lower than the second resolution, the second resolution is lower than the third resolution, and the first subset of layers of the neural network generates the second medical image based on an intrinsic physics-based model of a point spread function.

6. The method according to claim 5, wherein the intrinsic physics-based model of the point spread function is a spatially-variant model.

7. The method according to claim 6, wherein the spatially-variant model is a Gaussian-based model.

8. The method according to claim 5, wherein the second subset of layers of the neural network is based on a convolutional neural network.

9. A non-transitory computer-readable storage medium storing computer-readable instructions that, when executed by a computer, cause the computer to perform a method for enhancing computed tomography image resolution, comprising:
- receiving a first medical image having a first resolution;
- applying a neural network to the first medical image, the neural network including a first subset of layers and, subsequently, a second subset of layers, the first subset of layers of the neural network generating, from the first medical image, a second medical image having a second resolution and the second subset of layers of the neural network generating, from the second medical image, a third medical image having a third resolution; and
- outputting the third medical image,
- wherein the first resolution is lower than the second resolution, the second resolution is lower than the third resolution, and the first subset of layers of the neural network generates the second medical image based on an intrinsic physics-based model of a point spread function.

10. The non-transitory computer-readable storage medium according to claim 9, wherein the intrinsic physics-based model of the point spread function is a spatially-variant model.

11. The non-transitory computer-readable storage medium according to claim 10, wherein the spatially-variant model is a Gaussian-based model.

12. The non-transitory computer-readable storage medium according to claim 9, wherein the second subset of layers of the neural network is based on a convolutional neural network.

* * * * *